United States Patent
Holubec

(10) Patent No.: US 10,226,418 B2
(45) Date of Patent: Mar. 12, 2019

(54) ARGININE-CONTAINING TOPICAL COMPOSITION

(71) Applicant: SUSIE Q, LTD., Allen, TX (US)

(72) Inventor: Jerry T. Holubec, Allen, TX (US)

(73) Assignee: Susie Q, LTD., Allen, TX (US)

(*) Notice: Subject to any disclaimer, the term of this patent is extended or adjusted under 35 U.S.C. 154(b) by 328 days.

(21) Appl. No.: 14/275,465

(22) Filed: May 12, 2014

(65) Prior Publication Data

US 2015/0320710 A1  Nov. 12, 2015

(51) Int. Cl.
| | | |
|---|---|---|
| *A61K 31/198* | (2006.01) | |
| *A61K 9/00* | (2006.01) | |
| *A61K 31/455* | (2006.01) | |
| *A61K 36/31* | (2006.01) | |
| *A61K 36/185* | (2006.01) | |
| *A61K 31/4375* | (2006.01) | |
| *A61K 36/534* | (2006.01) | |
| *A61K 36/258* | (2006.01) | |
| *A61K 47/10* | (2017.01) | |
| *A61K 47/12* | (2006.01) | |

(52) U.S. Cl.
CPC ......... *A61K 9/0034* (2013.01); *A61K 9/0014* (2013.01); *A61K 31/198* (2013.01); *A61K 31/4375* (2013.01); *A61K 31/455* (2013.01); *A61K 36/185* (2013.01); *A61K 36/258* (2013.01); *A61K 36/31* (2013.01); *A61K 36/534* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 4,804,674 A | 2/1989 | Curtis-Prior et al. | |
| 6,007,824 A | 12/1999 | Duckett et al. | |
| 6,207,713 B1 | 3/2001 | Fossel | |
| 6,277,884 B1 | 8/2001 | de Tejada | |
| 6,322,493 B1 | 11/2001 | Thompson | |
| 6,323,241 B1 | 11/2001 | Yeager et al. | |
| 6,338,862 B1 | 1/2002 | Niazi | |
| 6,428,791 B1 | 8/2002 | Lezdey et al. | |
| 6,444,237 B1 | 9/2002 | Heleen | |
| 6,514,536 B2 | 2/2003 | Drizen et al. | |
| 6,548,545 B1 | 4/2003 | Thompson | |
| 6,702,733 B1 | 3/2004 | Thompson | |
| 6,737,084 B2 | 5/2004 | Crosby et al. | |
| 6,803,060 B2 | 10/2004 | Reyes | |
| 6,989,163 B2 | 1/2006 | Thompson et al. | |
| 7,048,941 B2 | 5/2006 | Altaffer et al. | |
| 7,128,932 B2 | 10/2006 | Bombardelli et al. | |
| 7,214,390 B2 | 5/2007 | Barone, Jr. et al. | |
| 7,229,649 B2 | 6/2007 | Wuh et al. | |
| 7,875,299 B2 | 1/2011 | Crosby et al. | |
| 8,063,104 B2 | 11/2011 | Vallance et al. | |
| 8,128,972 B2 | 3/2012 | Crosby et al. | |
| 8,287,926 B2 | 10/2012 | Bombardelli | |
| 2002/0004529 A1* | 1/2002 | Neal | A61K 9/0034 514/573 |
| 2002/0013280 A1 | 1/2002 | Xin | |
| 2002/0028257 A1* | 3/2002 | Catalfo | A61K 8/25 424/727 |
| 2003/0064123 A1 | 4/2003 | Thompson | |
| 2003/0077296 A1 | 4/2003 | Denton et al. | |
| 2007/0081967 A1* | 4/2007 | Cerullo | A61K 8/34 424/74 |
| 2009/0004294 A1* | 1/2009 | Margulies | A61K 9/0034 424/649 |
| 2009/0054497 A1* | 2/2009 | Ahmad | A61K 31/455 514/356 |
| 2009/0092687 A1 | 4/2009 | Stein | |
| 2009/0092696 A1 | 4/2009 | Burke et al. | |

FOREIGN PATENT DOCUMENTS

| | | | |
|---|---|---|---|
| WO | WO2003047610 A1 | 6/2003 | |
| WO | WO2006021930 A2 | 3/2006 | |
| WO | WO 2012145609 A1 * | 10/2012 | ............... A61K 8/44 |

* cited by examiner

*Primary Examiner* — Terry A McKelvey
*Assistant Examiner* — Catheryne Chen
(74) *Attorney, Agent, or Firm* — Dunlap Codding, P.C.

(57) ABSTRACT

A composition for topical application to a mucosal body site contains a combination of L-arginine, niacin, and a cooling compound. In one embodiment the composition contains from about 2% to about 7% by weight of a nitric oxide releasing substance selected from the group consisting of L-arginine, L-arginine salts and L-arginine derivatives. The composition also contains from about 0.05% to about 0.5% by weight niacin, and from about 0.1% to about 1% by weight of at least one compound capable of providing a sensation of cooling to the body site of application.

18 Claims, No Drawings

ARGININE-CONTAINING TOPICAL COMPOSITION

BACKGROUND OF THE INVENTIVE CONCEPTS

1. Field of the Inventive Concepts

The inventive concepts disclosed and claimed herein relate generally to a composition for topical application on mucosal areas of the human body, and more particularly, but not by way of limitation, to a topical composition that can be used to enhance female sexual activity.

2. Brief Description of Related Art

Topical compositions containing vasodilating compounds are known to enhance sexual activity in some individuals. The terms "vasodilation" and "vasodilatation" refer to the widening of blood vessels resulting from relaxation of smooth muscle cells within the vessel walls, in particular in the large veins, large arteries, and smaller arterioles. This results in enhanced blood circulation.

There are three main intracellular stimuli that can result in the vasodilation of blood vessels. Hyperpolarization-mediated or calcium channel blocker mechanisms, cAMP-mediated mechanisms which result in increasing calcium removal from the cytoplasm, and cyclic guanosine monophosphate (cGMP) mediated mechanisms commonly referred to as nitrovasodilation. Specific mechanisms to accomplish these effects vary from vasodilator to vasodilator.

Unfortunately, vasodilating compounds, when applied topically, can also cause irritation and their concentration on sensitive areas must be limited. In fact, certain homeopathic compounds which can improve circulation where applied actually work by way of irritation and cannot be used in the genitalia area. It would be useful if a composition having increased concentrations of vasodilating compounds could be topically applied to the genitalia area without significant irritation. It is to such a composition that the presently disclosed and claimed inventive concepts are directed.

SUMMARY OF THE INVENTIVE CONCEPTS

A composition for topical application to a mucosal body site contains a combination of L-arginine, niacin, and a cooling compound. In one embodiment the composition contains from about 2% to about 7% by weight of a nitric oxide releasing substance selected from the group consisting of L-arginine, L-arginine salts and L-arginine derivatives. The composition also contains from about 0.05% to about 0.5% by weight niacin, and from about 0.1% to about 1% by weight of at least one compound capable of providing a sensation of cooling to the body site of application.

In another embodiment, a composition for topical application to a mucosal body site includes a) from about 2% to about 7% by weight L-arginine; b) from about 0.05% to about 0.5% by weight niacin; c) from about 0.1% to about 0.5% by weight peppermint oil; and d) from about 0.1 to about 1.5% by weight vinpocetine.

In yet another embodiment, a method for enhancing female sexual activity includes the step of applying a topical composition to the female genitalia. The topical composition includes from about 2% to about 7% by weight L-arginine, from about 0.05% to about 0.5% by weight niacin, and from about 0.1% to about 1% by weight of at least one compound that provides a cooling sensation where applied.

DETAILED DESCRIPTION OF EXEMPLARY EMBODIMENTS

Before explaining at least one embodiment of the inventive concepts disclosed herein in detail, it is to be understood that the inventive concepts are not limited in their application to the details of construction, experiments, exemplary data, and/or the arrangement of the components set forth in the following description. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The presently disclosed and claimed inventive concepts include a composition for topical application to a body site containing a combination of one or more nitric oxide-releasing compounds such as L-arginine, L-arginine salts and L-arginine derivatives. The composition also includes niacin and a cooling compound. In one embodiment, the composition contains from about 2% to about 7% by weight L-arginine, L-arginine salts or L-arginine derivatives; from about 0.05% to about 0.5% by weight niacin; and from about 0.1% to about 1% by weight of at least one compound capable of providing a cooling sensation to the body site of application.

L-arginine is an amino acid synthesized in the body and supplemented to a lesser extent through diet. Among other useful roles in the body, L-arginine has been found to decrease blood pressure and increase blood flow by increasing nitric oxide (NO). Nitric oxide is the substance that relaxes the blood vessels, allowing for increased blood flow. It is a powerful vasodilator and is biosynthesized endogenously from L-arginine, oxygen, and NADPH by various nitric oxide synthase (NOS) enzymes. The inner lining of blood vessels uses nitric oxide to signal the surrounding smooth muscle to relax, thus resulting in vasodilation and increased blood flow.

Nonlimiting examples of suitable compounds providing L-arginine include D,L-arginine, L-arginine, alkyl (ethyl, methyl, propyl, isopropyl, butyl, isobutyl, t-butyl) esters of L-arginine and salts thereof. Pharmaceutically acceptable salts include, but are not limited to, hydrochloride, glutamate, butyrate, and glycolate.

In one embodiment, the composition for topical application to a body site includes from about 4% to about 6.5% by weight L-arginine. These higher concentrations of L-arginine are typically not well tolerated on mucosal tissues in genital areas, but can be well tolerated in the presently disclosed compositions as discussed in detail hereinafter.

Niacin, or nicotinic acid, has been used orally since the 1950s as a lipid-altering therapy to raise high-density lipoprotein cholesterol (HDL-C) levels. The major adverse experience limiting the more widespread use of niacin is cutaneous vasodilation resulting in flushing. This is a histamine reaction that results in increased blood flow to your skin and can result in "itchiness" and irritation.

Unlike L-arginine, niacin is rapidly absorbed from the skin. Because niacin is so readily absorbed, it can act as an excellent delivery system by rapidly dilating the blood vessels to provide better access for the L-arginine. However, mucosal tissues in the genital area can tolerate only limited concentrations of niacin without becoming uncomfortably irritated.

In one embodiment, the composition for topical application to a body site includes from about 0.1% to about 0.3% by weight niacin. It was discovered that these higher concentrations of niacin, as well as the higher concentrations of L-arginine, can be well tolerated by sensitive mucosal tissues when a cooling agent is included in the composition.

In one embodiment, the compound used to provide cooling is derived from a plant or herb. One such suitable compound that can provide a cooling sensation is peppermint oil. For example, the composition for topical application to a body site can include from about 0.2% to about 0.5% by weight peppermint oil. Peppermint oil is believed to activate cold-sensitive receptors in the skin and mucosal tissues, thereby providing the cooling sensation that follows topical application of the peppermint oil.

In one embodiment, the composition for topical application to a body part additionally includes vinpocetin in an amount from about 0.1% to about 2% by weight of the composition. Vinpocetin is an extract from the periwinkle plant and is sometimes marketed as a supplement for vasodilation and as a potent anti-inflammatory agent.

In one embodiment, the composition for topical application to a body part additionally includes maca root powder. *Lepidium meyenii*, known commonly as maca, is a herbaceous biennial plant of the crucifer family native to the high Andes of Peru. Maca (*Lepidium meyenii*) is the only member of its genus with a fleshy hypocotyl, which is fused with the taproot to form a rough inverted-pear-shaped body. It is grown for this fleshy hypocotyl which is used as a root vegetable, a medicinal herb, and as an aphrodisiac. Maca root powder is described by some to be similar to "natural" progesterone. Maca appears to stimulate the body to produce its own hormones more adequately rather than supplying hormones from an outside source. In this respect, maca root powder acts as a sexual stimulant when applied to the mucosal tissues of female genital areas.

In one embodiment, the composition for topical application to a body part additionally includes tongkat ali. *Eurycoma longifolia*, known commonly as tongkat ali, is a flowering plant native to Indonesia, Malaysia, and neighboring countries. The plant has been traditionally used for its antimalarial, aphrodisiac, anti-diabetic, antimicrobial and antipyretic properties. It is believed that tongkat ali (*Eurycoma longifolia*) has the capacity to reverse the inhibitory effects of estrogen on testosterone production and spermatogenesis. In this respect, tongkat ali can act as a sexual stimulant when applied to the mucosal tissues of female genital areas.

The presently disclosed compositions are effective in all types of vehicles. Non-limiting examples of suitable vehicles include emulsions, creams, lotions, solutions (both aqueous and hydro-alcoholic), gels, oils, and ointments or other vehicles as would be known to one of ordinary skill in the art.

Non-limiting examples of additional compounds and agents that can be used with the compositions of the presently disclosed compositions include lubricants, surfactants and emulsifiers, emulsion stabilizers, creaming agents, disinfectants and preservatives, antimicrobial agents, flavoring agents, scents, pigments, and the like.

EXAMPLES

The following examples are included to demonstrate preferred embodiments of the invention. It should be appreciated by those of skill in the art that the compositions disclosed in the examples which follow represent compositions discovered by the inventor to function well in the practice of the invention. However, those skilled in the art will appreciate that many changes can be made in the specific embodiments which are disclosed without departing from the spirit and scope of the invention.

Example 1

A topical composition was prepared by mixing in a laboratory mixer. The composition was found to provide enhanced female sexual activity. The composition is shown below in Table 1.

TABLE 1

Composition of Example 1

| Ingredients | Wt Percent |
| --- | --- |
| L-Arginine | 3.0 |
| Niacin | 0.1 |
| Peppermint Oil | 0.3 |
| Vinpocetine | 0.5 |
| Tongkat Ali | 0.5 |
| Maca Root Powder | 0.5 |
| *Ganoderma Lucidum* | 0.0001 |
| Horny Goat Weed | 0.5 |
| Aloe | 0.01 |
| Glycerin | 6.0 |
| Cetearyl alcohol and glucoside | 6.0 |
| Stearic acid | 3.0 |
| Cetyl and Behenyl Alcohols | 2.0 |
| Lecithins | 0.5 |
| Moisturizers | 2.5 |
| Polyhexamethylene biguanide | 1.0 |
| Water | Balance |

Example 2

The topical composition shown in Table 2 was prepared by mixing in a laboratory mixer. This composition was found to provide additional sexual enhancement compared to the composition of Example 1.

TABLE 2

Composition of Example 2

| Ingredients | Wt Percent |
| --- | --- |
| L-Arginine | 6.0 |
| Niacin | 0.25 |
| Peppermint Oil | 0.3 |
| Vinpocetine | 0.5 |
| Tongkat Ali | 0.5 |
| Maca Root Powder | 0.5 |
| *Ganoderma Lucidum* | 0.0001 |
| Horny Goat Weed | 0.5 |
| Aloe | 0.01 |
| Glycerin | 6.0 |
| Cetearyl alcohol and glucoside | 6.0 |
| Stearic acid | 3.0 |
| Cetyl and Behenyl Alcohols | 2.0 |
| Lecithins | 0.5 |
| Moisturizers | 2.5 |
| Polyhexamethylene biguanide | 1.0 |
| Water | Balance |

Example 3

A study was performed to determine the efficacy of niacin 0.25% in the sexual enhancement formula of this patent application. Fifty female subjects were randomly selected. The criteria of patient selection used to select the subject is the subject must not have had a hysterectomy or be menopausal. If the subject had a hysterectomy or was menopausal, the subject must be taking bio identical hormone replacement during this study.

Sexual enhancement samples were randomly set up as a double blinded study. Each subject was given two samples labeled A and B. The subjects did not know which sample contained 0.25% niacin and which sample was without niacin. In addition, the investigators did not know which sample contained 0.25% niacin and which sample did not contain niacin. The actual compositions of the samples are shown in Table 3 below.

TABLE 3

Compositions in Double Blinded Study of Example 3

| CTFA* NAME | COMPOSITION WITH NIACIN, % | COMPOSITION WITHOUT NIACIN, % |
| --- | --- | --- |
| WATER | 67.369 | 67.619 |
| ORGANIC *ALOE BARBADENSIS* LEAF JUICE | 0.010 | 0.010 |
| GLYCERIN | 6.000 | 6.000 |
| HYDROXYPROPYLCELLULOSE | 1.500 | 1.500 |
| ORGANIC SOY LECITHIN | 0.300 | 0.300 |
| *HELIANTHUS ANNUUS* (SUNFLOWER) SEED OIL | 1.000 | 1.000 |
| CETEARYL ALCOHOL | 2.000 | 2.000 |
| COCO-CAPRYLATE/CAPRATE | 3.500 | 3.500 |
| CETYL ALCOHOL | 1.000 | 1.000 |
| STEARIC ACID | 3.000 | 3.000 |
| CETEARYL ALCOHOL & CETEARYL GLUCOSIDE | 4.000 | 4.000 |
| BEHENYL ALCOHOL | 1.000 | 1.000 |
| HYDROGENATED LECITHIN | 0.200 | 0.200 |
| L-ARGININE | 6.000 | 6.000 |
| *LEPIDIUM MEYENII* ROOT EXTRACT | 0.500 | 0.500 |
| PROPYLENE GLYCOL & WATER & *EPIMEDIUM SAGITTATUM* (HORNY GOAT) EXTRACT | 0.500 | 0.500 |
| *EURYCOMA LONGIFOLIA* ROOT EXTRACT | 0.010 | 0.010 |
| *GANODERMA LUCIDUM* (MUSHROOM) POWDER | 0.001 | 0.001 |
| *COLEUS FORSKOHLII* ROOT EXTRACT | 0.010 | 0.010 |
| *VINCA MINOR* (PERIWINKLE) EXTRACT | 0.500 | 0.500 |
| POLYAMINOPROPYL BIGUANIDE | 1.000 | 1.000 |
| FLAVOR | 0.050 | 0.050 |
| *MENTHA PIPERITA* (PEPPERMINT) OIL | 0.300 | 0.300 |
| NIACIN | 0.250 | 0.000 |
| TOTAL | 100.000 | 100.000 |

*Names adopted by the CTFA (Cosmetics, Toiletries, and Fragrance Association)

Samples labeled A or B were individually selected to contain 0.25% niacin or not contain niacin; i.e. some samples labeled A contained 0.25% niacin and some samples labeled A contained no niacin. Therefore, twenty five subjects had sample A containing 0.25% niacin in the sexual enhancement formula and twenty five subjects had sample A containing no niacin in the sexual enhancement formula. In the subject samples without niacin, the remaining percentages equaling 100% were made up with water. The subjects used the samples over a weekend. On Saturday, they used one of the samples with or without the niacin in the sexual enhancement formula. On Sunday, the next day, they used the other sample they were given. They were told to rate their results immediately after sexual activity for efficacy of the formula causing sexual enhancement.

The ratings were designated as Greatly Superior, Somewhat Superior, Equal to the other formula, and Less than equal to the other formula. Results were tallied using the double blind formula correction correlating the samples to the 0.25% niacin or non-niacin containing samples.

Results: 48 out of the 50 subjects (96%) rated the sexual enhancement formula with 0.25% niacin as Greatly Superior in the study compared to using the formula without niacin. Only 2 subjects (4%) rated the sexual enhancement formula with 0.25% niacin as Somewhat Superior to using the Non-niacin formula. No subjects rated the Non-niacin formula Greatly Superior, Somewhat superior, or Equal to the 0.25% niacin formula.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished without departing from the scope of the inventive concepts disclosed herein and defined by the appended claims.

What is claimed is:

1. A composition for topical application to mucosal tissues in female genital areas, the composition in a form selected from the group consisting of creams, lotions, gels, and ointments, the composition comprising a nitric oxide releasing substance, niacin, at least one compound that provides a cooling sensation when applied to mucosal tissues, and water, wherein:
   a) the nitric oxide releasing substance is selected from the group consisting of L-arginine, L-arginine salts and L-arginine derivatives and is present at from about 2% to about 7% by weight of the composition;
   b) the niacin is present at from about 0.05% to about 0.5% by weight of the composition; and
   c) the at least one compound that provides a cooling sensation comprises peppermint oil and is present at from about 0.1% to about 1% by weight of the composition.

2. The composition of claim 1, comprising from about 4% to about 6.5% by weight L-arginine.

3. The composition of claim 1, comprising from about 0.1 to about 0.3% by weight niacin.

4. The composition of claim 1, comprising about 0.2% to about 0.5% by weight peppermint oil.

5. The composition of claim 1, further comprising from about 0.1% to about 2% by weight vinpocetine.

6. The composition of claim 1, further comprising at least one compound having at least one of a testosterone promoting property and an estrogen suppressing property.

7. The composition of claim 1, further comprising maca root powder.

8. The composition of claim 1, further comprising tongkat ali.

9. A composition for topical application to mucosal tissues in female genital areas, the composition comprising a mixture in a form selected from the group consisting of creams, lotions, gels, and ointments, the mixture comprising:
   a) from about 2% to about 6.5% by weight L-arginine;
   b) from about 0.05% to about 0.5% by weight niacin;
   c) from about 0.1% to about 0.5% by weight peppermint oil; and
   d) from about 0.1 to about 1.5% by weight vinpocetine; wherein
   the niacin and the nitric oxide releasing substance are better tolerated by the mucosal tissues in female genital areas compared to the same composition without the at least one compound that provides a cooling sensation.

10. The composition of claim 9, further comprising from about 0.1% to about 1% by weight maca root powder.

11. The composition of claim 9, further comprising from about 0.1% to about 1% by weight tongkat ali.

12. A method for enhancing female sexual activity, the method comprising: applying a topical composition to the female genitalia, the composition comprising from about 2% to about 7% by weight L-arginine, from about 0.05% to about 0.5% by weight niacin, and from about 0.1% to about 1% by weight peppermint oil.

13. The method of claim 12, wherein the topical composition comprises from about 4% to about 6.5% by weight L-arginine.

14. The method of claim 12, wherein the topical composition comprises from about 0.1% to about 0.3% by weight niacin.

15. The method of claim 12, wherein the at least one compound that provides a cooling sensation comprises peppermint oil.

16. The method of claim 15, wherein the topical composition comprises from about 0.2% to about 0.5% by weight peppermint oil.

17. The method of claim 15, wherein the topical composition further comprises from about 0.1% to about 2% by weight vinpocetin.

18. The method of claim 15, wherein the topical composition further comprises maca root powder and tongkat ali.

* * * * *

UNITED STATES PATENT AND TRADEMARK OFFICE
CERTIFICATE OF CORRECTION

PATENT NO.       : 10,226,418 B2
APPLICATION NO.  : 14/275465
DATED            : March 12, 2019
INVENTOR(S)      : Jerry T. Holubec It is certified that error appears in the above-identified patent and that said Letters Patent is hereby corrected as shown below:

On the Title Page

Under abstract "18 Claims, 0 Drawing Sheets" should read 17 Claims, 0 Drawing Sheets In the Claims Column 6 Line 64-Column 8 Line 32 should be corrected to read:
1. A composition for topical application to mucosal tissues in female genital areas, the composition in a form selected from the group consisting of creams, lotions, gels, and ointments, the composition comprising a nitric oxide releasing substance, niacin, at least one compound that provides a cooling sensation when applied to mucosal tissues, and water, wherein:
    a) the nitric oxide releasing substance is selected from the group consisting of L-arginine, L-arginine salts and L-arginine derivatives and is present at from about 2% to about 7% by weight of the composition;
    b) the niacin is present at from about 0.05% to about 0.5% by weight of the composition; and
    c) the at least one compound that provides a cooling sensation comprises peppermint oil and is present at from about 0.1% to about 1% by weight of the composition.

2. The composition of claim 1, comprising from about 4% to about 6.5% by weight L-arginine.

3. The composition of claim 1, comprising from about 0.1 to about 0.3% by weight niacin.

4. The composition of claim 1, comprising about 0.2% to about 0.5% by weight peppermint oil.

Signed and Sealed this
Eighth Day of October, 2019

Andrei Iancu
*Director of the United States Patent and Trademark Office*

5. The composition of claim 1, further comprising from about 0.1% to about 2% by weight vinpocetine.

6. The composition of claim 1, further comprising at least one compound having at least one of a testosterone promoting property and an estrogen suppressing property.

7. The composition of claim 1, further comprising maca root powder.

8. The composition of claim 1, further comprising tongkat ali.

9. A composition for topical application to mucosal tissues in female genital areas, the composition comprising a mixture in a form selected from the group consisting of creams, lotions, gels, and ointments, the mixture comprising:
    a) from about 2% to about 6.5% by weight L-arginine;
    b) from about 0.05% to about 0.5% by weight niacin;
    c) from about 0.1% to about .5% by weight peppermint oil; and
    d) from about 0.1 to about 1.5% by weight vinpocetine; wherein the niacin and the nitric oxide releasing substance are better tolerated by the mucosal tissues in female genital areas compared to the same composition without the at least one compound that provides a cooling sensation.

10. The composition of claim 9, further comprising from about 0.1% to about 1% by weight maca root powder.

11. The composition of claim 9, further comprising from about 0.1% to about 1% by weight tongkat ali.

12. A method for enhancing female sexual activity, the method comprising: applying a topical composition to the female genitalia, the composition comprising from about 2% to about 7% by weight L-arginine, from about 0.05% to about 0.5% by weight niacin, and from about 0.1% to about 1% by weight peppermint oil.

13. The method of claim 12, wherein the topical composition comprises from about 4% to about 6.5% by weight L-arginine.

14. The method of claim 12, wherein the topical composition comprises from about 0.1% to about 0.3% by weight niacin.

15. The method of claim 12, wherein the topical composition comprises from about 0.2% to about 0.5% by weight peppermint oil.

CERTIFICATE OF CORRECTION (continued)
U.S. Pat. No. 10,226,418 B2

16. The method of claim 12, wherein the topical composition further comprises from about 0.1% to about 2% by weight vinpocetin.

17. The method of claim 12, wherein the topical composition further comprises maca root powder and tongkat ali.